United States Patent
Jin et al.

(10) Patent No.: US 9,163,107 B2
(45) Date of Patent: Oct. 20, 2015

(54) CATIONIC POLYMERS FORMED FROM AMINO GROUP-BEARING MONOMERS AND HETEROCYCLIC LINKERS

(75) Inventors: Tuo Jin, Shanghai (CN); Shiyue Duan, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 88 days.

(21) Appl. No.: 13/977,973

(22) PCT Filed: Jan. 5, 2012

(86) PCT No.: PCT/CN2012/070055
§ 371 (c)(1),
(2), (4) Date: Jul. 29, 2013

(87) PCT Pub. No.: WO2012/092865
PCT Pub. Date: Jul. 12, 2012

(65) Prior Publication Data
US 2013/0310536 A1    Nov. 21, 2013

Related U.S. Application Data

(60) Provisional application No. 61/430,529, filed on Jan. 6, 2011.

(51) Int. Cl.
*C08G 12/06* (2006.01)
*C08G 73/02* (2006.01)
(Continued)

(52) U.S. Cl.
CPC .............. *C08G 12/06* (2013.01); *A61K 9/5031* (2013.01); *A61K 47/34* (2013.01); *C08G 73/0273* (2013.01); *C08G 73/18* (2013.01); *C12N 15/87* (2013.01)

(58) Field of Classification Search
CPC ................................ C08G 73/02; C08G 12/06
USPC .......................................... 528/423, 245, 246
See application file for complete search history.

(56) References Cited

U.S. PATENT DOCUMENTS

4,048,148 A    9/1977    Morgan
5,015,699 A    5/1991    Cotts et al.

FOREIGN PATENT DOCUMENTS

| CN | 102154349 A | 8/2011 |
|---|---|---|
| WO | WO 96/37194 A1 | 11/1996 |
| WO | WO 2009/100645 A1 | 8/2009 |

OTHER PUBLICATIONS

Jin et al; "Polycationic gene—and histidine", 2009; Patent, People. Rep. China; Chem Abstract 151: 297919.*

(Continued)

*Primary Examiner* — Duc Truong
(74) *Attorney, Agent, or Firm* — Knobbe, Martens, Olson & Bear, LLP

(57) ABSTRACT

The present invention is directed to a design of and a method to synthesize polycations for gene (DNA and RNA) delivery. According to this design, the polycations (also said cationic polymers) are formed by polymerization of endogenous monomers bearing sufficient amino groups through degradable bonds with linker molecules. The amino group-bearing monomers are those naturally existing or nontoxic to human body. The linker molecules are those which are not only degradable to nontoxic fragments but also able to release the amino group-bearing monomers in their native state upon degradation. Some examples for the endogenous amino group-bearing monomers are spermine and spermidine (or their derivatives). Examples for the degradable chemical bonds formed between the amino group-bearing monomers are imines. In order to improve degradability or proton sponging effect, low pKa (<8) amino group(s), free amino groups

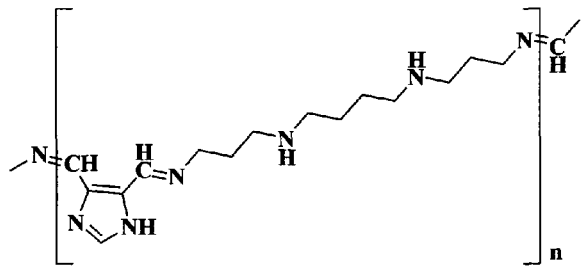

A: Polyspermine imidazole-4,5-imine

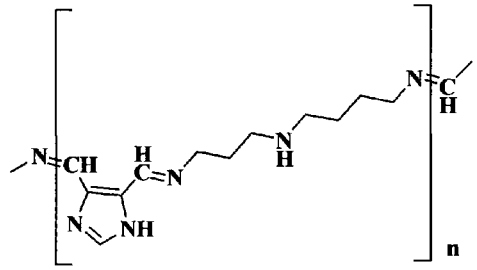

B: Polyspermidine imidazole-4,5-imine generated by polymer degradation (such as those generated by degradation of imine linkages), or other electron donating group(s) such as imidazole, pyrazole, pyridine, pyrimidine, or even benzene is incorporated in the linker between the two (or three) reactive groups for linking the amino group-bearing monomers. These polycationic carrier systems can be used for nano-encapsulation and transfection of gene materials.

12 Claims, 15 Drawing Sheets

(51) Int. Cl.
*A61K 9/50* (2006.01)
*A61K 47/34* (2006.01)
*C08G 73/18* (2006.01)
*C12N 15/87* (2006.01)
*C12N 11/08* (2006.01)
*A61K 47/30* (2006.01)
*A61K 48/00* (2006.01)

(56) References Cited

OTHER PUBLICATIONS

Supplementary European Search Report in European Application No. EP 12 73 2063 dated Nov. 12, 2014 in 5 pages.

* cited by examiner

A: Polyspermine imidazole-4,5-imine    B: Polyspermidine imidazole-4,5-imine

A: Polyspermine imidazole-2,5-imine    B: Polyspermidine imidazole-2,5-imine

A: Polyspermine pyrazole-3,4-imine    B: Polyspermidine pyrazole-3,4-imine

A: Polyspermine pyrazole-3,5-imine    B: Polyspermidine pyrazole-3,5-imine

A: Polyspermine pyridine-bis-imine    B: Polyspermidine pyridine-bis-imine

A: Polyspermine pyrimidine-bis-imine    B: Polyspermidine pyrimidine-bis-imine

A: Polyspermine benzene-bis-imine    B: Polyspermidine benzene-bis-imine

A: Polyspermine imidazole-4,5-imine

B: Polyspermidine imidazole-4,5-imine

A: Polyspermine imidazole-2,5-imine

B: Polyspermidine imidazole-2,5-imine

A: Polyspermine pyrazole-3,4-imine

B: Polyspermidine pyrazole-3,4-imine

A: Polyspermine pyrazole-3,5-imine

B: Polyspermidine pyrazole-3,5-imine

A

B

US 9,163,107 B2

CATIONIC POLYMERS FORMED FROM AMINO GROUP-BEARING MONOMERS AND HETEROCYCLIC LINKERS

CROSS REFERENCE AND RELATED APPLICATION

This application claims priority of U.S. Ser. No. 61/430,529 filed Jan. 6, 2011, the contents of which are incorporated by reference here into this application.

Throughout this application, reference is made to various documents including U.S. Ser. No. 12/843,691, Filed Jul. 26, 2010. The disclosures of these documents in their entireties are hereby incorporated by reference into this application to more fully describe the state of the art to which this invention pertains.

FIELD OF THE INVENTION

This invention pertains to a structure design and a synthetic method of cationic polymers useful as gene (DNA and RNA) carriers degradable to endogenous monomers and safety-known species.

BACKGROUND OF THE INVENTION

It has been sufficiently evident that poly- or oligonucleotides of sensible (sense and/or antisense) sequences can be used as effective therapeutic agents in drug therapy, vaccination and tissue regeneration by turning the relevant gene on (expression) or off (silencing)[1]. To achieve such therapeutic efficacy, however, therapeutic genes, DNA vaccines as well as siRNA drugs must be delivered to the nuclei or cytoplasm of target cells. Among the carrier systems for delivering polynucleotides (also named as gene, gene materials, oligonucleotides, nucleic acids hereafter or DNA and RNA), synthetic delivery systems possess a series of advantages over viral vectors such as freedom from immunity and viral mutation, ability to package multiple genes or siRNA of choice into particulate vehicles via a single mechanism, and adaptability to simple and cost-efficient manufacturing process[2]. To deliver gene materials (DNA and RNA) to targeted inter- and intra-cellular sites effectively using non-viral systems, the synthetic gene carriers (i.e. non-viral vectors) must accomplish a number of tasks consequently comprising (A) packing gene materials to nano-particulate forms to avoid pre-phagocytosis degradation, (B) attaching on targeted cells selectively, (C) facilitating endosomal escape of gene materials, (D) releasing gene materials in cytoplasm, and (E) metabolizing itself to nontoxic species. There is yet, however, a synthetic gene delivery system reported to date meets all these criteria.

Synthetic gene delivery vehicles reported in last decades can, in general, be divided into several categories, cationic liposome-based systems (called lipoplex), cationic polymer-based systems (called polyplex), lipid-cationic polymer combined systems (called lipopolyplex) and non-charged nanometer particulates. The majority of them are lipoplexes and polyplexes due to the negative charges of DNA and RNA by which the gene materials may easily be condensed into particles with positively charged liposomes or polymers. These two categories possess different advantages and mechanisms in terms of each step of gene transfection. Cationic liposomes condense gene materials less compactly than cationic polymers[3] but offer unique membrane fusion function with endosomes that may help DNA or RNA to escape to cytoplasm in molecular form[4]. Polycations (cationic polymer), on the other hand, may condense gene materials in more compacted forms[3] so that better protection and larger capacity of gene materials are expected[5]. For endosomal escaping, polyplex is believed to undergo a "proton sponging" process for which the polyplex-engulfing endosome is ruptured by chloride ions accumulated due to continuous influx pumping of HCl into endosomes to compensate the protons consumed by the cationic polymer carrier. In this case, the protonated polycation gains more positive charges to bind DNA or RNA due to which the gene materials enter cytoplasm in the form of particles rather than molecules. It has been reported that ruptured endosomes may be self-repaired so that the polyplex particle may be re-encapsulated before escaping[6]. In addition, the polynucleotides must be released or extracted out of the polyplex in order to exert their biological functions. It seems that condensation and release of DNA or RNA by polycations are a pair of contradictory processes which require a polycationic carrier system to be chemically dynamic and biologically responsive.

To compromise gene packing and release, some researchers suggested to use or design a polycationic carrier which possesses a mild strength of gene condensation[7]. Using a cationic polymer with low molecular weight or with low amino group density is one of the approaches[8]. Another strategy is to use environment responsive polycations to achieve gene condensation and releasing, the two opposite moves, consequently[9]. This type of polymers are, however, often complex in structures and complicated in metabolic process and metabolized products. Using degradable cationic polymers as gene carriers may be a more reasonable approach by which gene release may be achieved by degradation of the backbone of the carriers, a process independent of its ability to condense DNA or RNA[10]. Degradation to small molecules will reduce chemical toxicity of polycations. As reported in the literature, biodegradable linkages such as carboxylic ester, phosphate ester, imine or disulfide structure were incorporated in the backbone of a cationic polymers. In this aspect, ester bond is the most widely used degradable structure to incorporate into the polycation backbone for its balanced stability and degradability. However, ester bond is highly reactive to nucleophiles such as primary and secondary amino groups[11], which are the key functional groups for gene compacting and proton sponging. In addition, degradation of ester structures creates acids that compromise the proton-sponging effect.

Some researchers polymerized branched small molecular polyethylenimine (PEI) via an ester-bearing linker, and the cross-linked small molecular PEI carriers possess higher gene transfection efficiency but lower toxicity[14]. Backbone degradation of this polymer was achieved by cleavage of the linker, leaving the cleft fragments attached to the small molecular PEI or other amino group-bearing monomers (the polymer building blocks)[12-14]. Such a backbone degradation pattern may be fine for a polycationic gene carrier formed of man-made amino group-bearing building blocks. For a degradable cationic polymer formed of endogenous amino group-bearing monomers, the attachment of linker fragments upon polymer degradation will dismiss the advantages of using endogenous monomers. A polycationic gene carrier degradable to human endogenous amino group-bearing monomers is an ideal design to achieve intracellular release of genes and metabolic elimination of the carrier itself.

WO2009/100,645 disclosed a method to develop polycationic gene carriers which possess sufficient amount of amino groups to condense polynucleotides into compacted particles and to induce endosomal break through proton sponge effect[15], and possess fully degradable backbone to release polynucleotides after endosomal escape and to turn itself to endogenous or non-toxic metabolites.

SUMMARY OF THE INVENTION

As discussed above, a clinically useful delivery system should be capable to pack DNA or RNA of choice (single or multiple types) into nanoparticles with sufficient density, to target the polynucleotide-loading nanoparticles to diseased cells, to transport and release gene materials into cytoplasm of the cells, and finally, to degrade itself to nontoxic metabolites. For practical applications, the system should best be simple in structure, easy to prepare and formulate, and stable in storage, transportation and clinical operation. The above biological criteria may be translated into a series of required chemical properties of a synthetic polycationic carrier, comprising sufficient positive charges to pack negatively charged DNA or RNA, flexibility and easiness to conjugate or associate with targeting moieties to diseased cells, sufficient amount of low pKa (<8) amino groups as a pool for proton sponging, and degradability to non-toxic (preferably endogenous) monomers for intracellular release of polynucleotides, and ability to metabolize or be eliminated of their self.

The present invention discloses a design of chemical structures of cationic polymers of which a monomers bearing sufficient number of amino groups are polymerized as the basic building blocks with a linker molecule possessing an aromatic ring through a degradable linkage. The amino group-bearing monomers are best to be those naturally existing (endogenous) in or nontoxic to the human body. In order to improve degradability or proton sponging effect, the linker molecules are best to be those which possess a heterocyclic ring containaing nitrogen (or nitrogens) and a pKa not over 8. The linker molecule is best to link the amino group bearing monomers through conjugated imine structure. The imine linkage structure should be stable in a neutral environment (such as body fluid) but degradable responsively in an acidic environment (such as endosome or lyososome) and release the endogenous amino group-bearing monomer and the linker as their original states upon degradation. The responsively degradable linkage structures should also be best to conjugated π bonds so that it is sufficiently stable to prevent pre-cellular (pre-phagocytosis) degradation and dissociation of the polymer and the polyplex formed of the polymer and nucleic acids.

Some examples for the endogenous amino group-bearing monomers are spermine and spermidine (or their derivatives), and examples of the nitrogen-containing heterocyclic linkers are imidazole-4,5-dialdehyde, imidazole-2,5-dialdehyde, pyrazole-3,4-dialdehyde, pyrazole-3,5-dialdehyde, pyridine substituted with two formic aldehydes, and pyrimidine substituted with two formic aldehydes.

The said cationic polymers are chemically dynamic in order to degrade responsively to the pH differences along the delivery pathway from intercellular to cellular and from endosomes to lysosomes. To meet various delivery needs, chemical stability and pH responsibility may be adjusted by selecting linker molecules. For example, the poly-imine bonds formed with pyrazole-3,4-dialdehyde is more stable than that formed with imidazole-4,5-dialdehyde, and poly-imine bonds formed with pyridine or pyrimidine or benzene both substituted with two formic aldehydes are more stable than those formed with the other two linkers.

DETAILED DESCRIPTION OF THE INVENTION

Figure 1:
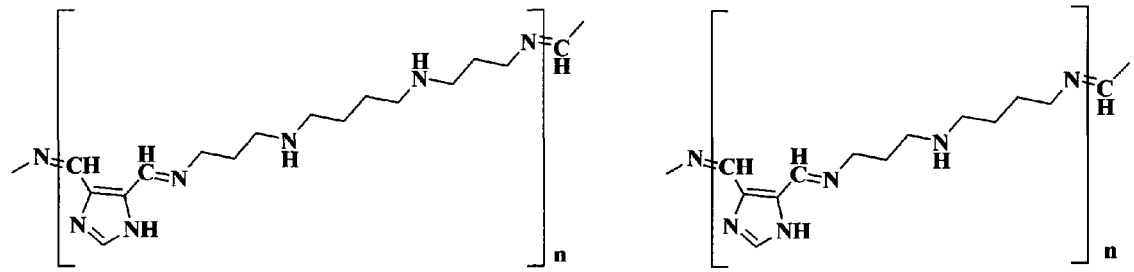
FIG. 1. The structures of (A) polyspermine imidazole-4,5-imine and (B) polyspermidine imidazole-4,5-imine.
Figure 2:
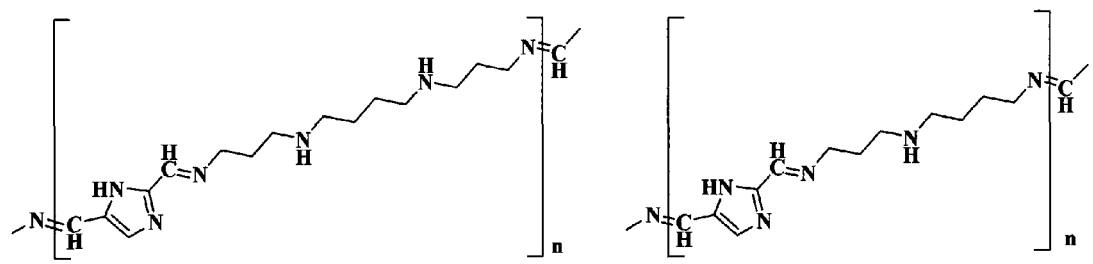
FIG. 2. The structures of (A) polyspermine imidazole-2,5-imine and (B) polyspermidine imidazole-2,5-imine.
Figure 3:
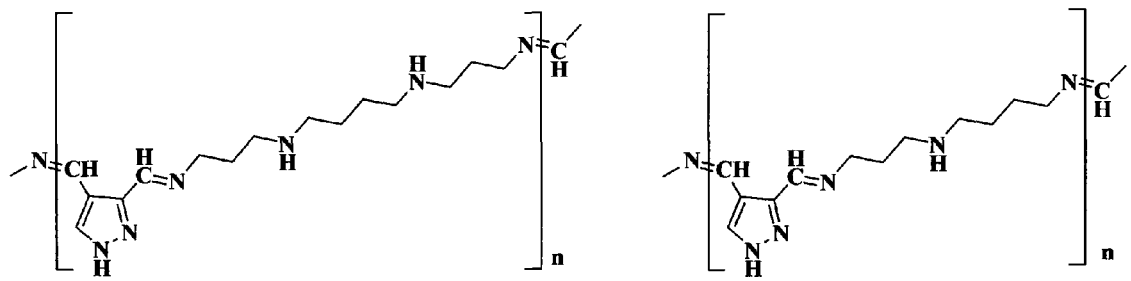
FIG. 3. The structures of (A) polyspermine pyrazole-3,4-imine and (B) polyspermidine pyrazole-3,4-imine.
Figure 4:
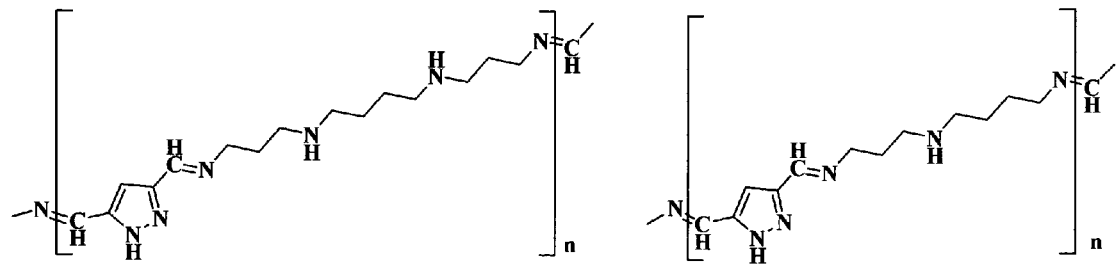
FIG. 4. The structures of (A) polyspermine pyrazole-3,5-imine and (B) polyspermidine pyrazole-3,5-imine.
Figure 5:
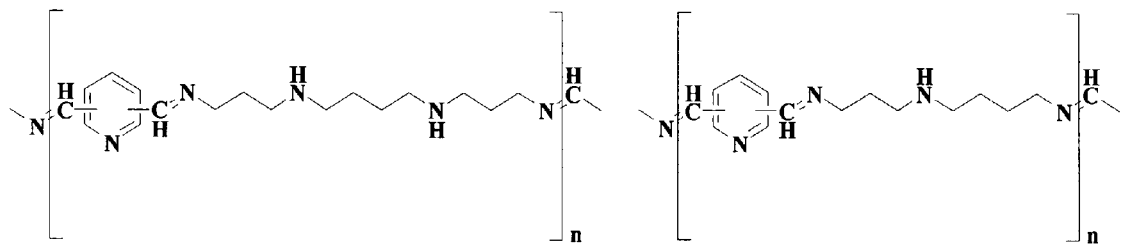
FIG. 5. The structures of (A) polyspermine pyridine-bis-imine and (B) polyspermidine pyridine-bis-imine.
Figure 6:
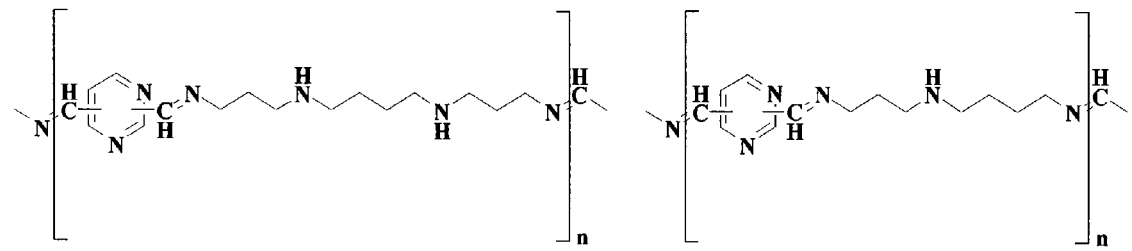
FIG. 6. The structures of (A) polyspermine pyrimidine-bis-imine and (B) polyspermidine pyrimidine-bis-imine.
Figure 7:
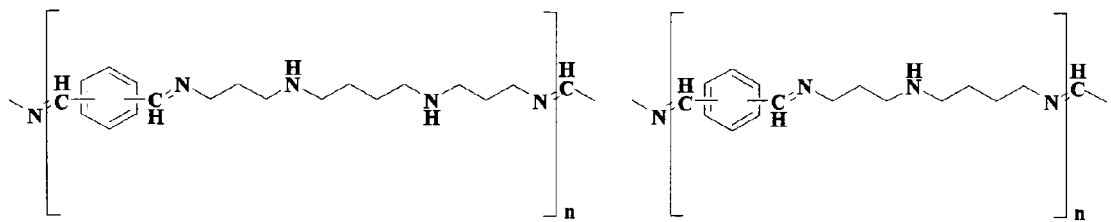
FIG. 7. The structures of (A) polyspermine benzene-bis-imine and (B) polyspermidine benzene-bis-imine.
Figure 8:
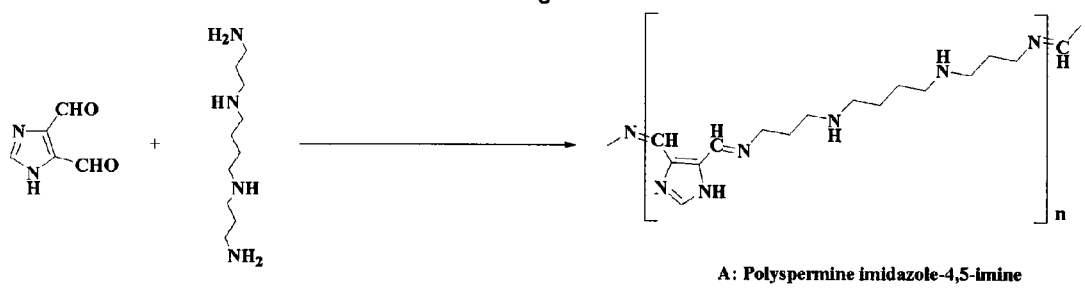
FIG. 8. The polymerization reaction schemes of (A) polyspermine imidazole-4,5-imine and (B) polyspermidine imidazole-4,5-imine.
Figure 8:
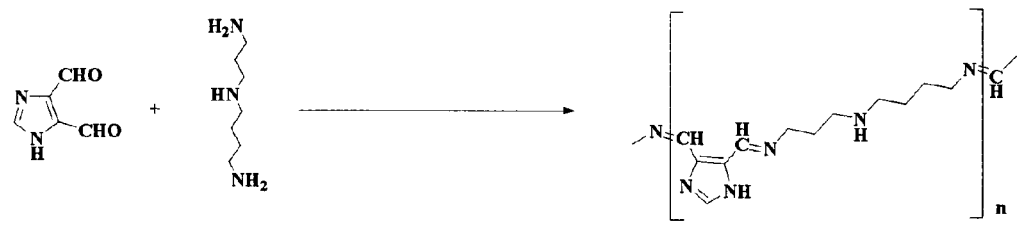
Figure 9:
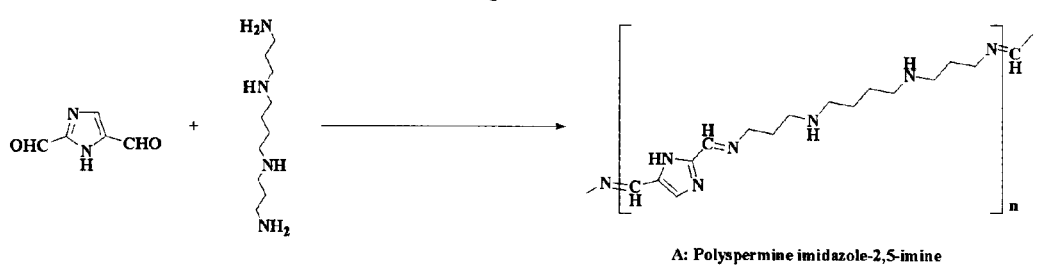
FIG. 9. The polymerization reaction schemes of (A) polyspermine imidazole-2,5-imine and (B) polyspermidine imidazole-2,5-imine.
Figure 9:
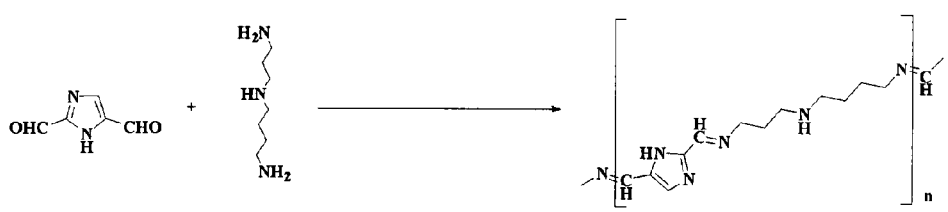
Figure 10:
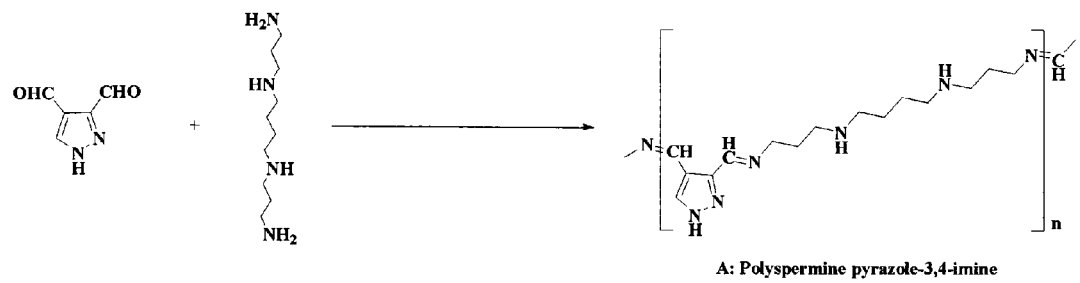
FIG. 10. The polymerization reaction schemes of (A) polyspermine pyrazole-3,4-imine and (B) polyspermidine pyrazole-3,4-imine.
Figure 10:
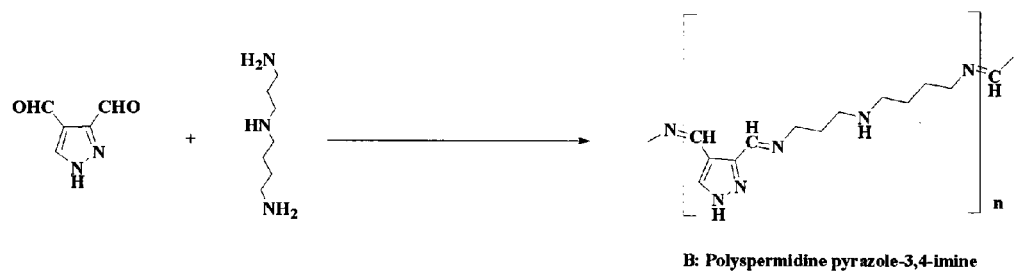
Figure 11:
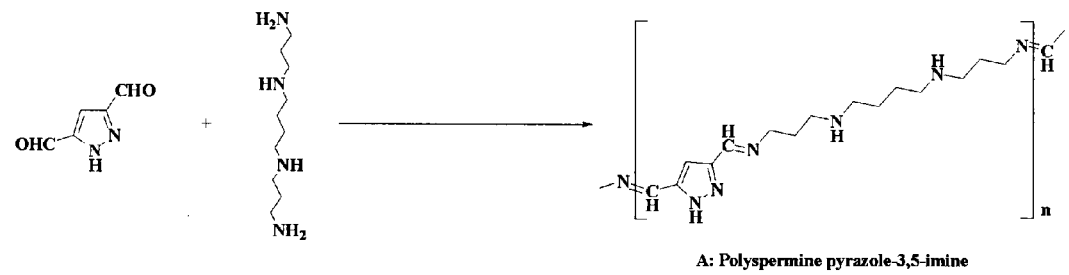
FIG. 11. The polymerization reaction schemes of (A) polyspermine pyrazole-3,5-imine and (B) polyspermidine pyrazole-3,5-imine.
Figure 11:
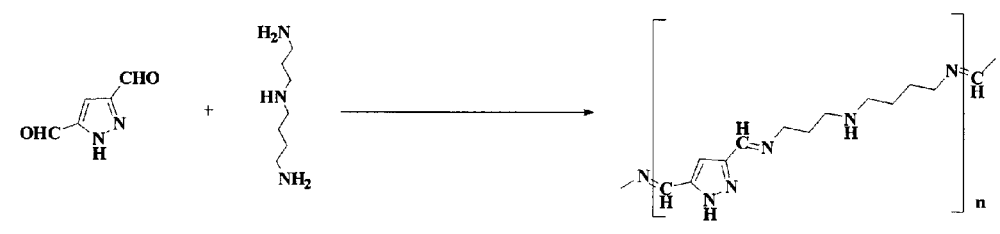
Figure 12:
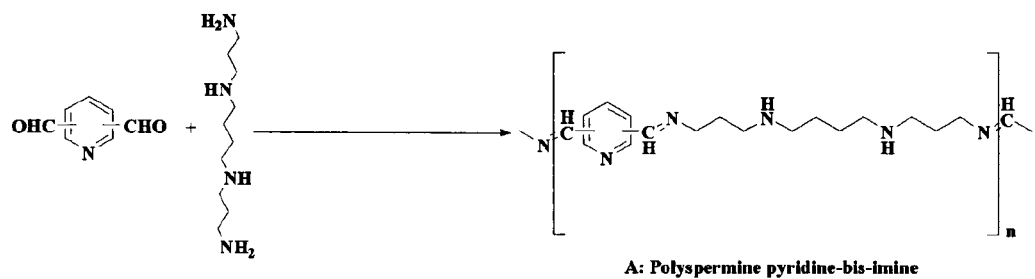
FIG. 12. The polymerization reaction schemes of (A) polyspermine pyridine-bis-imine and (B) polyspermidine pyridine-bis-imine.
Figure 13:
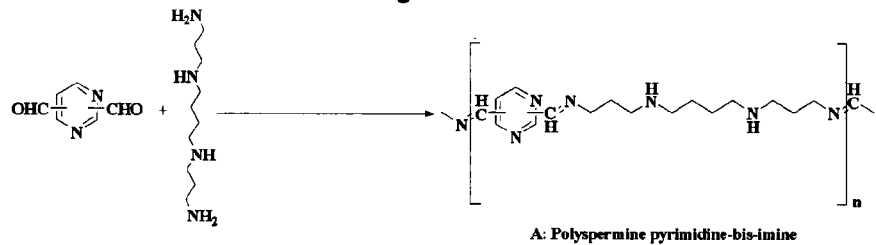
FIG. 13. The polymerization reaction schemes of (A) polyspermine pyrimidine-bis-imine and (B) polyspermidine pyrimidine-bis-imine.
Figure 14:
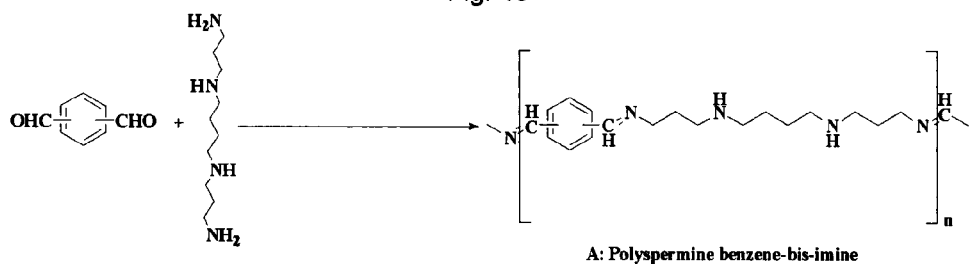
FIG. 14. The polymerization reaction schemes of (A) polyspermine benzene-bis-imine and (B) polyspermidine benzene-bis-imine.

Effective gene delivery requires a delivery system to accomplish a series of biological functions comprising condensing genes into compacted particles, carrying genes into target cells, helping genes to escape endosomal degradation, releasing genes into cytoplasm, and degrading the delivery system into monomers non-toxic to and able to be eliminated from the body. To meet these requirements, a synthetic gene delivery system must possess respective functional groups to exert these biological functions. From practical aspects, such as synthesis, formulation and toxicity study, it is also important that such a multi-functional synthetic gene carrier must be structurally simple.

One embodiment of the gene carrier system of the present invention consists of a type of cationic polymers of which endogenous amino group-bearing monomers, spermine and/or spermidine, are incorporated as the basic building block. Spermine or spermidine was polymerized with a linker molecule through a degradable linkage which is fairly stable in body fluid, but degrades in response to endosomal pH and release the endogenous amino group-earing monomer as its original state. One of the linkage structures able to meet such criteria is conjugated imine. For example, a bis-aldehyde possessing a conjugated π bond may be used as the linker by reacting with the primary amines of spermine or spoermidine to form polyspermine imines or polyspermidine imines. It will be even more super if the conjugated π structure of the linker possesses a pKa below 7 or 8 so that the endosomal pH will protonate the conjugated π bond and disrupt the linkage. A bis-aldehyde conjugated with an aromatic ring, especially a nitrogen-containing heterogeneous ring, is such an idea linker molecule.

Gene materials (DNA or RNA) can be condensed into particles simply by mixing a solution of the nucleic acids with an aqueous solution of the cationic polymers at appropriate amino groups (from the polymer) to phosphate groups (from the nucleic acids) ratio. Gene transfection, anti-sense effect or RNA interferon effect can be achieved by adding this gene carrier suspension into cell medium. The polycations help polynucleotides to enter cells, escape from endosomes, and be released into cytoplasm.

The cationic polymers possess great capability and convenience in condensing polynucleotides into nano-particulate simply by mixing them with selected therapeutic nucleic acids, large or small as well as single type or multiple types of genes. The poly-linked spermine or spermidine polymers may function as gene condenser, proton sponge, and responsive-release gene carrier. During the process exerting these functions, the polymers self-metabolize to non-toxic species.

Another advantage of the linked spermine (or spermidine) polymers in addition to lowering toxicity is that their degradation does not generate acidic groups like other degradable polymers. Rather, their degradation generates free amino groups that help to further buffer the acidity inside endosomes and facilitate endosome rupture. Hiding the proton-absorbing amino groups in mine form helps to break endosome and release polynucleotides into cytoplasm without causing high Zeta potential, a key factor to shorten in vivo circulation time and interrupt inter-cellular targeting.

For proton sponge effect, the endosome is broken by osmotic pressure generated by proton sponging effect (absorption of protons). Amino groups of the polycations are responsible for proton absorption. However, increase in amino group in cationic polymer (i.e. N/P ratio) will also lead to positive surface charges of polyplex which reduces circulation time of the polynucleotide-carrying particles in the body due to the negative charge of tissue surfaces. In the present invention, the nitrogen-containing linkages do not contribute to positive surface charge when it condenses with gene materials, but offer acid buffering effect when they degrade in endosomes and release free amino groups after being taken by cells. This nature helps the polynucleotide-carrying particles to achieve the same endosomal escape effect with lower surface charge and ensures better cell targeting.

The present invention provides a cationic polymer comprising a plurality of amin-group-bearing monomers linked by linkers via cleavable and pH responsible bonds. The amino group bearing monomers may be human endogenous amines or their derivatives. In one embodiment of the invention, the amino group-bearing monomers are selected from spermine, spermidine and their combinations thereof. In one embodiment of the invention, the cleavable bonds can be cleaved to release said amino-group-bearing monomers.

In another embodiment of the invention, the cleavable bonds are imines. In the above-mentioned cationic polymer, the linkage structure between repeating units of the polymers comprise amino groups with pKa<8. In one embodiment, these linkages are conjugated with an aromatic ring, especially a nitrogen-containing heterocyclic ring. This nitrogen-containing heterocyclic ring is selected from imidazole, pyrazole, pyridine and pyrimidine. The poly-imine structures conjugated with these four types of heterocyclic ring possess different degradability and stability to meet the delivery needs. The spermine- (or spermidine-) containing polymer poly-linked with a conjugated an imidazole ring is more pH-responsible than the other three, and that poly-linked with a pyridine ring or a pyrimidine is more stable than the other two.

The present invention also provides a method of synthesizing the above-mentioned cationic polymer, comprising a reaction between the amino group-bearing monomers and the linkers possessing two or three reactive groups, or a reaction between said amine monomers. The said reactive groups may be aldehydes. For example, the said cationic polymer may be formed by condensation reaction between spermine (or spermidine) and imidazole bis- (or di-) aldehyde, pyrazole bis- (or di-) aldehyde, pyridine bis- (or di-) aldehyde, pyrimidine bis- (or di-) aldehyde, or phthalic aldehydes. However, condensation between spermine or spermidine and bis- (or di-) aldehyde is not the sole approach to synthesize the claimed cationic polymer based on a poly-imine structure involving a comjugated aromatic ring, especially a nitrogen-containing heterocyclic ring.

The present invention further teaches a use of the cationic polymer to encapsulate and deliver a DNA or RNA into polyplexes (nano-particulates). The amino group-bearing monomers (i.e. the basic building blocks) can be selected from any molecules possessing at least two primary amino groups. Some good examples are spermine and spermidine, two endogenous amino group-bearing molecules condensing with nucleotides in sperms. The linker molecules are those possessing a nitrogen-containing heterocyclic ring and at least two functional groups able to form imine (>C=N—) structures with the primary amino groups of the building blocks. Some examples of the linker molecules are imidazole-4,5-bisaldehyde, imidazole-2,5-bisaldehyde, pyrazole-3,4-bisaldehyde, pyrazole-3,5-bisaldehyde, pyridine substituted with two formic aldehydes, pyrimidine substituted with two formic aldehydes, and phthalic aldehydes.

When these two amino group-bearing building blocks and the four heterocyclic linkers are paired one by one and allowed to polymerize, eight (8) ABABAB . . . types of polymers may be formed. FIGS. 1, 2, 3 and 4 show the molecular structures of these polymers formed through the four linkers, respectively. The reaction schemes for forming these polymers from the paired building blocks and the linkers are depicted in FIGS. 5, 6, 7 and 8.

Since each of the amino group-bearing monomer (spermine or spermidine) possesses two primary amino groups and each of the linker (imidazole-4,5-bisaldhyde, imidazole-2,5-bisaldehyde, pyrazole-3,4-bisaldehyde, pyrazole-3,5-bisaldehyde, pyridine substituted with two formic aldehydes, pyrimidine substituted with two formic aldehydes, or phthalic aldehydes) possesses two aldehyde groups, one-by-one pairing between the building blocks and the linkers will lead to linear polymers. For those amino group-bearing monomers and aldehyde-possessing linkers which have more than two functional groups, branched polymers may be formed. Also, as long as the conjugate π bond structures of the heterocyclic linkers remain, substitution of the available =CH— site and the >N—H site of the rings is acceptable (for forming the polymers).

The most unique characteristics of the above-described polymers are their degradability responded to endosomal pH as well as the pattern of the degradation products which are endogenous monomers and safety-known monomers. The nitrogen-containing heterocyclic linkage structures have the capability to absorb protons; consequently, their conjugate π bond system will be interrupted and the polymeric linkages become unstable. This nature enables the above-described polymers to respond to the low pH environment of endosomes and lysosomes of cells which engulfing the nanoparticulate (celled polyplex), and readily degrade. The each linkage of the polymers being engulfed (with the polyplex) will absorb proton pumped into endosomes to degrade, and release two more free amino groups which absorb two more protons. Absorption of protons in endosomes or lysosomes is called "proton sponging" effect, a known mechanism to rupture these intracellular vesicles and release polynucleotides into the cytoplasm of cells.

This invention also provides a method of synthesizing a cationic polymer, comprising a reaction between an amino group-bearing monomer and a linker possessing two or more reactive groups. In one embodiment, the reactive groups are aldehydes.

This invention also provides a method to encapsulate and deliver a DNA or RNA, or to assemble lipid bilayers around polypex through intermolecular interactions.

Examples

Following examples are aimed to help technologists of related disciplines to better understand this invention. The examples should not be used to limit the applications and rights of this invention.

Example 1

Synthesis of Polyspermine Imidazole-4,5-Imine (See FIG. 8A)

In a three-necked flask (250 ml) equipped with a dropping funnel, 1.05 equivalent spermine was dissolved in anhydrous DMF (5 ml), to which 0.00625 equivalent p-Toluenesulfonic acid monohydrate and a small amount of freshly activated molecular sieves of type 4A were added at room temperature under a high-purity nitrogen atmosphere. 1.0 equivalent 1H-Imidazole-4,5-dicarboxaldehyde dissolved in anhydrous DMF (5 ml) was added dropwise to the mixture slowly over 4 hours, and heated quickly to 80° C. After stirring for another 24 hours, the solution was filtrated in vacuum and evaporated to remove the solvent. The viscous residue was dissolved again in water and dialyzed through a cellulose membrane of molecular weight cutoff of 10000 for 24 hours to remove the small fragments. The dialysate was stored at −80° C. for 4 hours and then freeze-dried over 24 hours to obtain water-soluble yellowish products as solid.

Example 2

Figure 15:
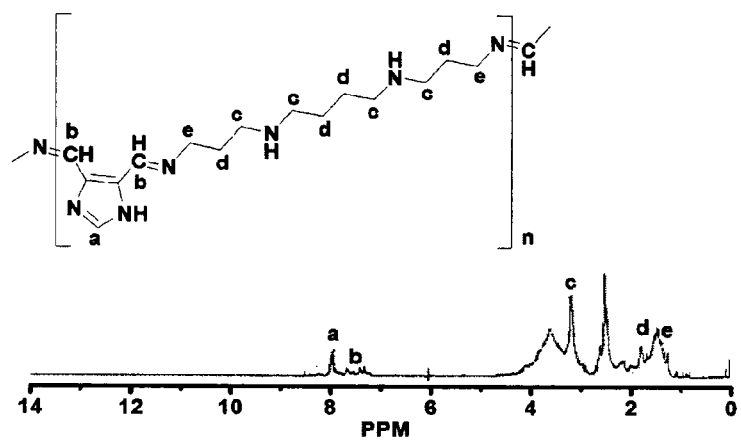
FIG. 15. $^1$H-Nuclear magnetic resonance (NMR) and $^{13}$C-NMR spectrum of polyspermine imidazole-4,5-imine (DMSO-d6).
Figure 15:
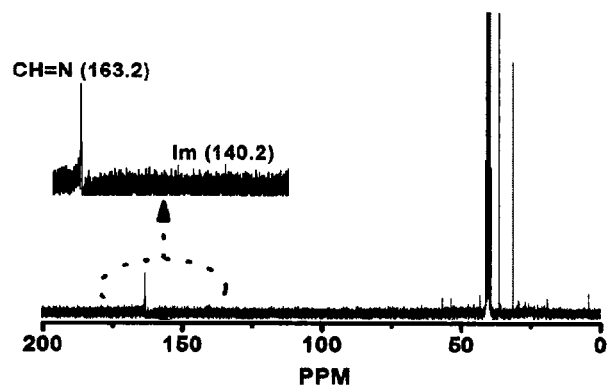
Figure 16:
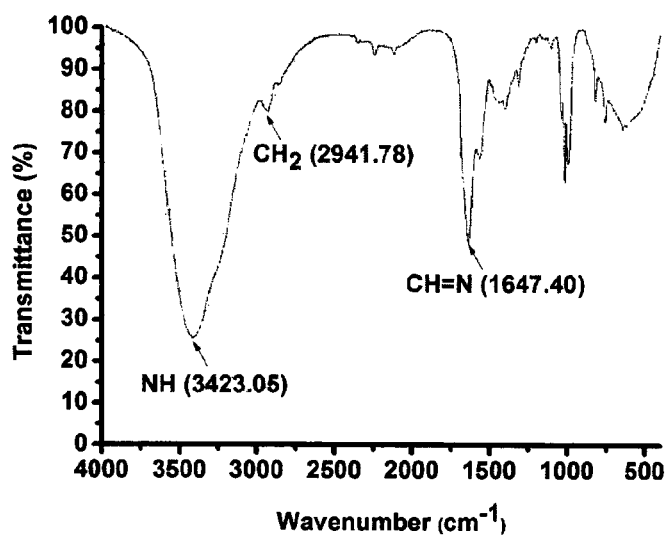
FIG. 16. Fourier Transform Infrared (FT-IR) spectrum of polyspermine imidazole-4,5-imine (within a KBr disk).
Figure 17:
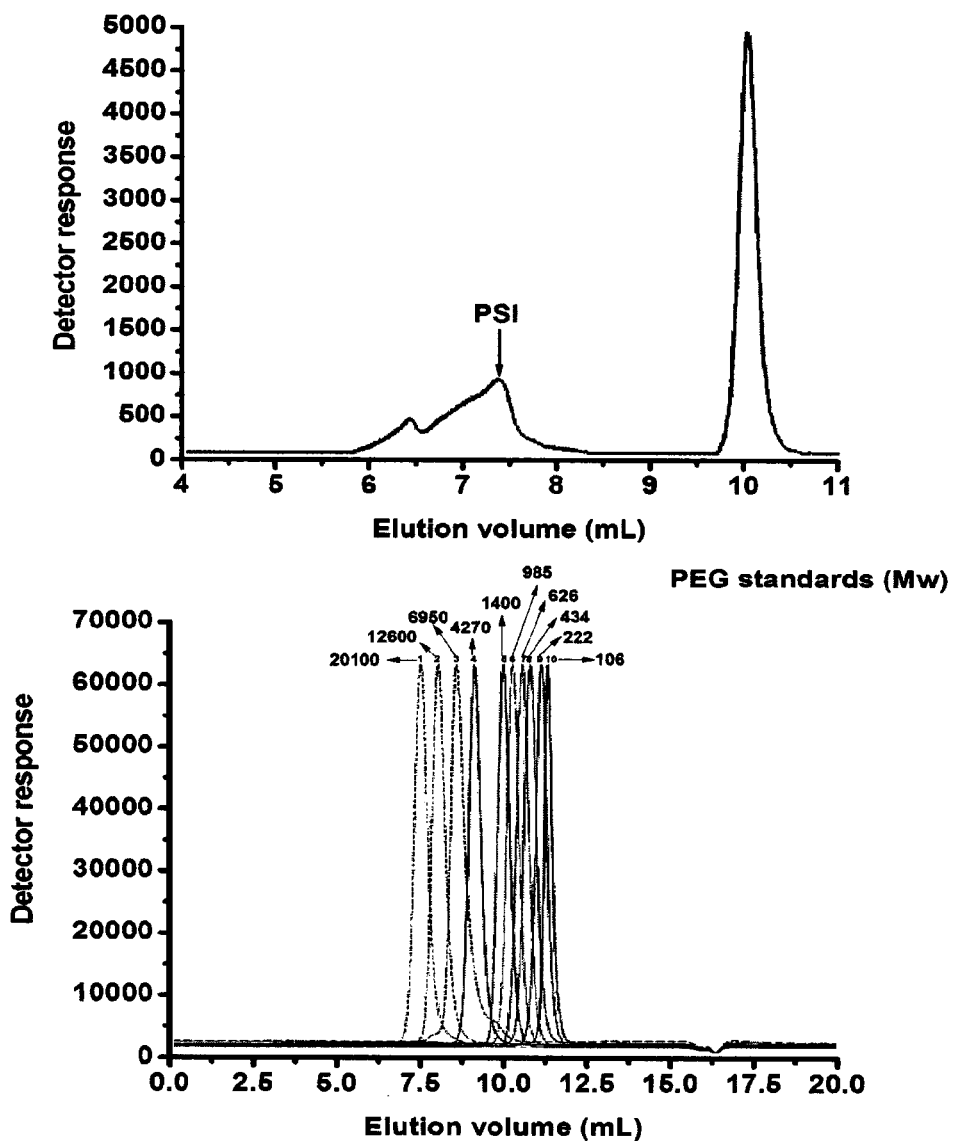
FIG. 17. SEC HPLC charts of polyspermine imidazole-4,5-imine in water (PEG as standards).

Structural Characterization of Polyspermine Imidazole-4,5-Imine $^1$H-NMR and $^{13}$C-NMR spectrum of polyspermine imidazole-4,5-imine was dissolved in DMSO-$d_6$ with 0.03% (v/v) tetramethylsilane (TMS) as internal standard. Results of the measurement were shown in FIG. 15; FT-IR spectrum of polyspermine imidazole-4,5-imine compressed with KBr into a disk was recorded using a Bruker Optics FT-IR spectrometer. A spectrum recorded in the range of 400-4000 cm$^{-1}$, at resolution of 4 cm$^{-1}$ for 16 scans accumulation is shown in FIG. 16. Molecular weight of obtained polyspermine imidazole-4,5-imine was determined using an Agilent 1260 Infinity equipped with a size exclusion chromatography (SEC-HPLC) column, a diode array detector (DAD), and refractive

Example 3

Degradation of Polyspermine Imidazole-4,5-Imine Under Various pH

Figure 18:
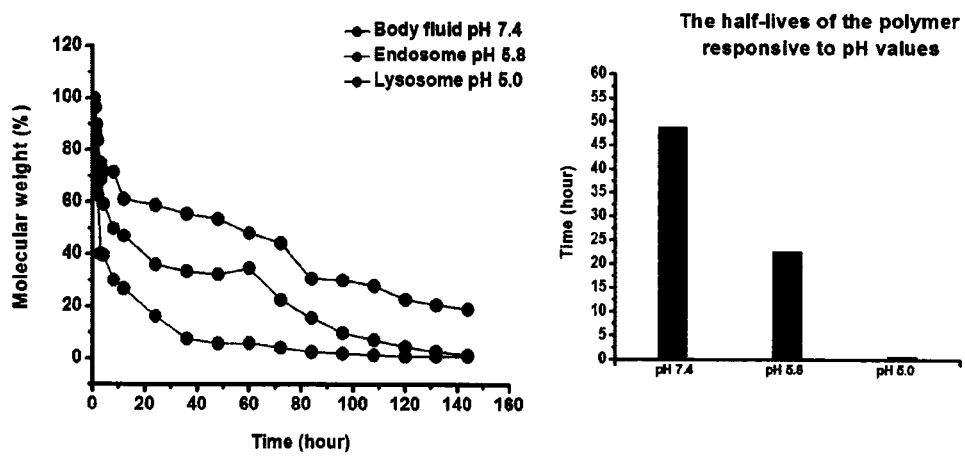
FIG. 18. The degradation curves and the half-lives (the time needed for the average molecular weight of the polymer to drop to half of their original) of polyspermine imidazole-4,5-imine in formic buffers at different pH.

Polyspermine imidazole-4,5-imine was dissolved in formic buffers to concentration of 2.0 mg/ml under pH 7.4, 5.8 and 5.0, the simulates of body fluid, endosomes and lysosomes. The polymers to be characterized (for molecular weight) were incubated under the respective pH at 37° C., and sampled for SEC-HPLC measurement. The degradation rates of the polymers were determined by the molecular weight changes measured by SEC-HPLC (relative to PEG standard). As shown in FIG. 18, degradation rates of polyspermine imidazole-4,5-imine under the three various pH were remarkably different from each other. The time for the polymer to drop their molecular weight to the half of the original under pH 7.4, 5.8 and 5.0 were 48, 21, and 1 hours, respectively (See the insert of FIG. 18).

Example 4

Figure 19:
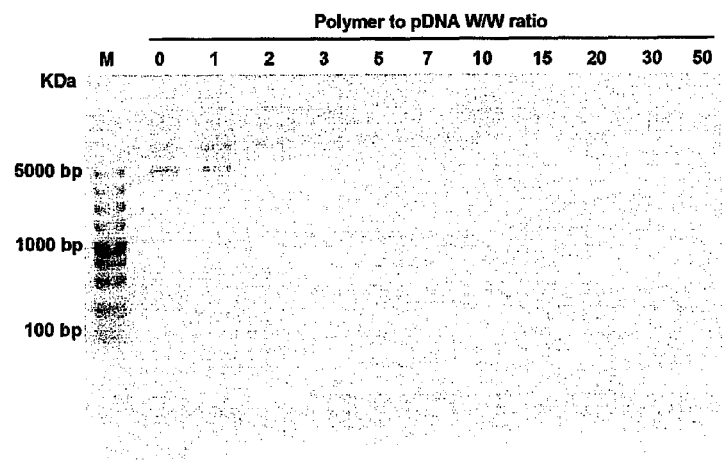
FIG. 19. Agarose gel electrophoresis of polyplexes formed of polyspermine imidazole-4,5-imine and pDNA at various WAN ratios in water.
Figure 20:
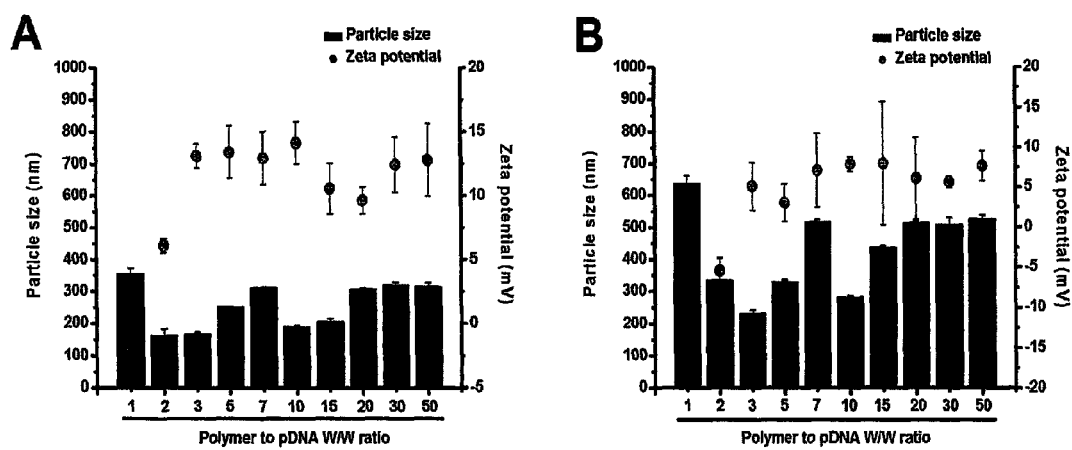
FIG. 20. Particle size and Zeta potential of polyplexes formed of polyspermine imidazole-4,5-imine and pDNA at various polymer to gene ratios (W/W) in water and pH 7.0 HEPES buffer (0.05 mol/L).
Figure 21:
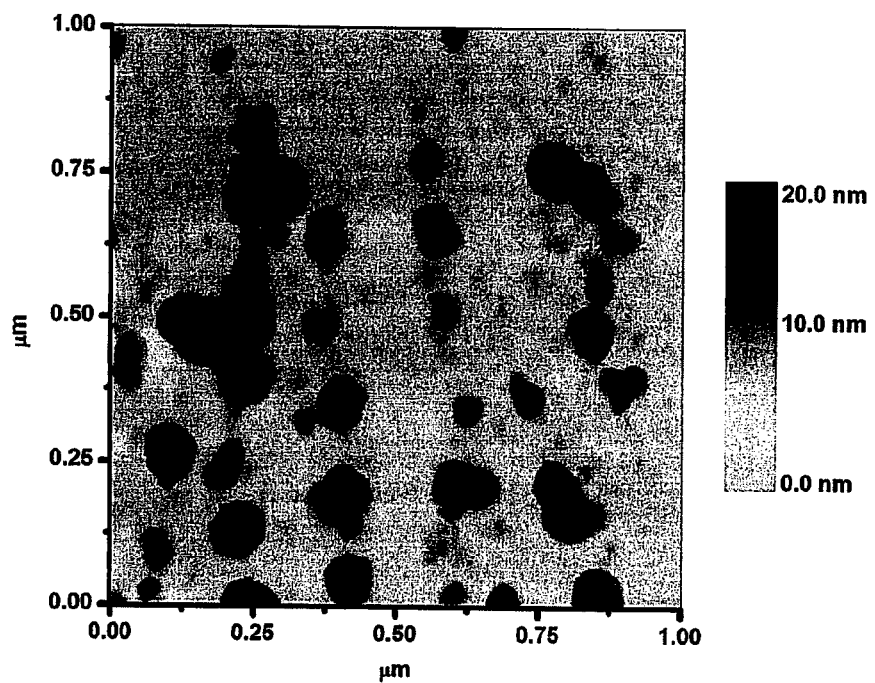
FIG. 21. AFM image of polyplexes formed of polyspermine imidazole-4,5-imine and pDNA when the polymer to gene ratio (W/W) was 2.
Figure 22:
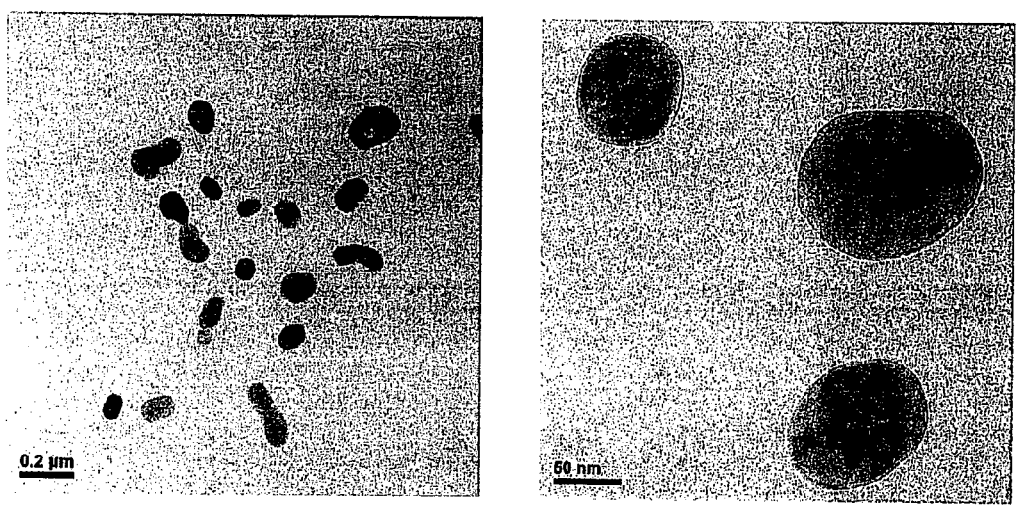
FIG. 22. TEM images of polyplexes formed of polyspermine imidazole-4,5-imine and pDNA when the polymer to gene ratio (W/W) was 2.

Preparation and Characterization of Polyplexes Formed of Polyspermine Imidazole-4,5-Imine and Luciferase pGL3-Control Plasmid Polyplexes were formed by mixing polyspermine imidazole-4,5-imine into pDNA solution at various polymer to gene ratio (W/W), followed 30 min maturing at room temperature. The formed polyplexes were loaded on a 1.0% agarose gel in 1× Tris-Acetate-EDTA (TAE) buffer containing 0.5 µg/ml ethidium bromide with 6× loading buffer and subjected to electrophoresis for 45 mins at 110 V. The retardation of pDNA electrophoresis was visualized using a UV illuminator. As shown in FIG. 19, the electrophoresis of pDNA was completely retarded when the polymer to gene ratio (W/W) reached 3 or over. The particle size and Zeta potential of the polyplexes at various polymer to gene ratios were measured in water and HEPES buffer (pH 7.0; 0.05 M) using a Brookhaven Particle Size Analyzer (90 Plus). The mean values of particle sizes and Zeta potential (±standard deviations) shown in FIG. 20 were calculated from three experiments. Morphology of the polyplexes formed at polymer to gene ratio of 2 was imaged using an Atomic Force Microscope (AFM, Nanoscope IIIa AFM system, Veeco, USA) and shown in FIG. 21. Transmission electron microscopic (TEM) images of the same polyplexes were taken using an JEM 2010 system (JEOL, Japan) and shown in FIG. 22. The polyplex sizes measured using the two methods are comparable (around 100-200 nm).

Example 5

Figure 23:
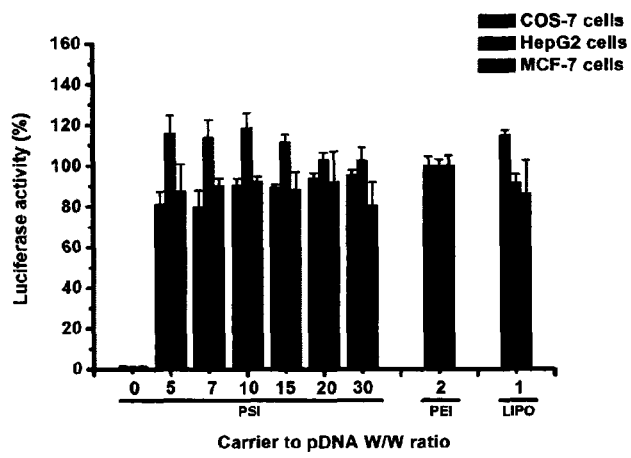
FIG. 23. Activity of polyplexes formed of polyspermine imidazole-4,5-imine and pDNA in transfecting luciferase gene in COS-7 cells, HepG2 cells, and MCF-7 cells at at various polymer to gene ratios (W/W).

Transfection Efficiency of Polyplexes Formed of Polyspermine Imidazole-4,5-Imine and Luciferase pGL3-Control Plasmid COS-7 cells, HepG2 cells, and MCF-7 cells were maintained in Dulbecco's modified Eagle's medium (DMEM) supplemented with 10% (v/v) fetal bovine serum (FBS), 100 units/ml penicillin and 100 µg/ml streptomycin at 37° C. in a 5% $CO_2$ humidified atmosphere. For gene transfection, COS-7 cells, HepG2 cells, and MCF-7 cells were seeded in a 48-well plate at a density of $5 \times 10^4$ cells per well to reach about 90% confluent at the time of transfection and incubated for 24 hours. pDNA (500 ng) was added in a polyspermine imidazole-4,5-imine solution at various W/W ratios of polymer to gene to form polyplexes. PEI 25 KDa and Lipofectamine 2000 were used as references at W/W ratio of 2 and 1, respectively. The carrier-gene complexes were incubated with the cells in the OPTIMEM I medium (Invitrogen) for 4 hours. The transfection medium was then replaced by fresh medium and incubated for additional 48 hours. Finally, the transfected cells were washed with PBS solution and lysed with 1× cell lysis buffer (Promega), followed by centrifugation at 12000 rpm for 3 mins. To determine gene expression activity, 20 µl supernatant was mixed with 20 µl substrate (Luciferase Assay System, Promega) and its luminescence was measured using a single tube luminometer (Berthold Detection Systems). Gene transfection activity of polyspermine imidazole-4,5-imine and the two references was defined as the luminescence per unit protein whose amount was determined using Micro BCA™ Assay Kit (Thermo Scientific Pierce). To cancel the variation due to cell conditions, relative expression activity (with that of PEI-25 KD as 100%) are shown in FIG. 23.

Example 6

Figure 24:
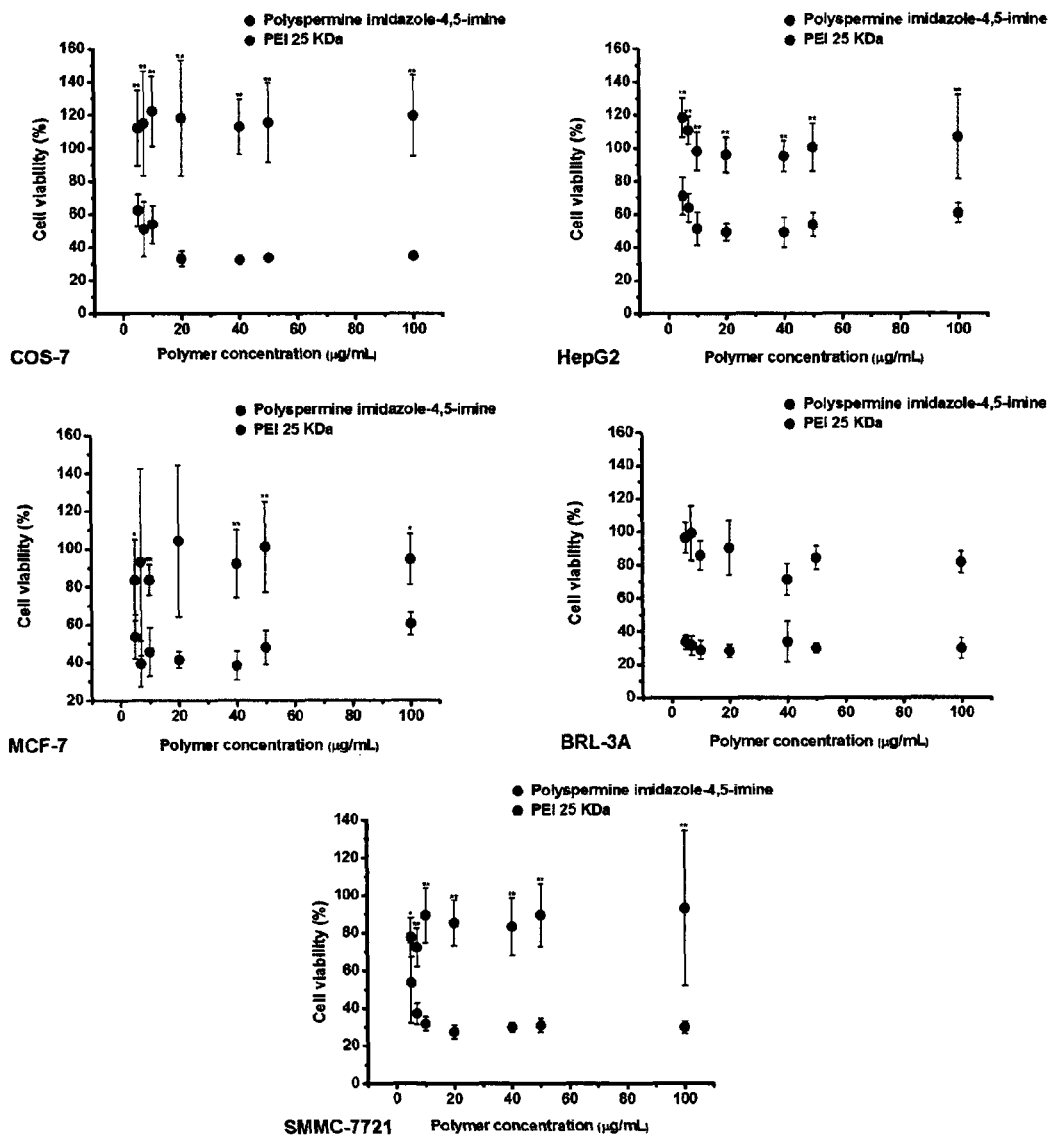
FIG. 24. Viability of COS-7 cells, SMMC-7721 cells (stably expressing the GL3 luciferase gene), HepG2 cells, MCF-7 cells, and BRL-3A cells treated with polyspermine imidazole-4,5-imine and PEI 25 KDa at various polymer concentrations (*: $P<0.05$; **: $P<0.01$).
Figure 25:
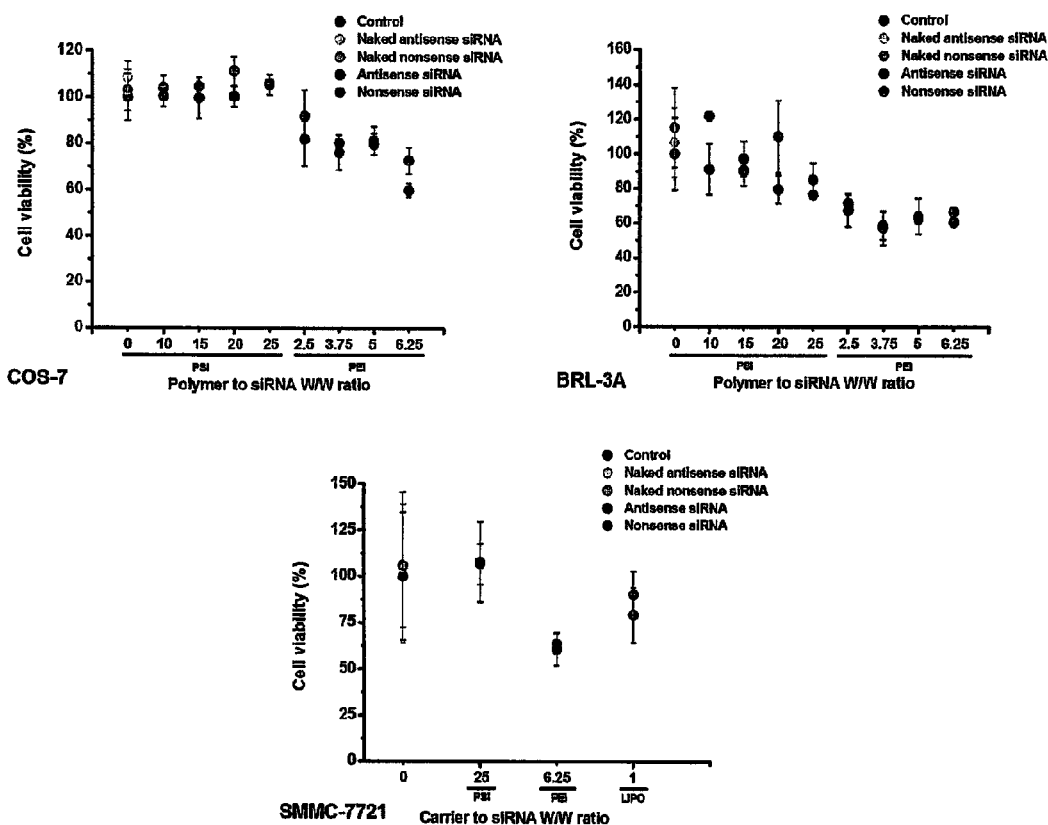
FIG. 25. Viability of COS-7 cells, BRL-3A cells, and SMMC-7721 cells (stably expressing the GL3 luciferase gene) treated with polyplexes formed of polyspermine imidazole-4,5-imine, PEI 25 KDa, or Lipofectamine 2000 and siRNA at various polymer to gene ratios (W/W).
Figure 26:
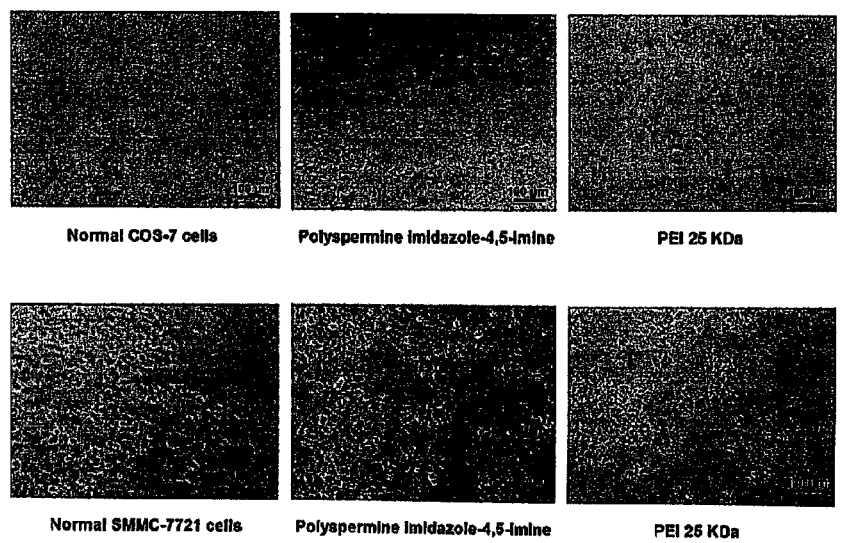
FIG. 26. Microscopic images of COS-7 cells and SMMC-7721 cells stably expressing the GL3 luciferase gene treated with polyspermine imidazole-4,5-imine or PEI 25 KDa at the concentration of 100 µg/ml.

Cytotoxicity of Polyspermine Imidazole-4,5-Imine and Polyplexes Formed of Polyspermine Imidazole-4,5-Imine and siRNA Cytotoxicity of polyspermine imidazole-4,5-imine in comparison with PEI 25 KDa was evaluated by percent viability of variety of cell lines, comprising COS-7, is SMMC-7721 cells stably expressing the GL3 luciferase gene, HepG2, MCF-7, and BRL-3A cells. For MTT assay, COS-7 cells, SMMC-7721 cells, HepG2 cells, MCF-7 cells, and BRL-3A cells were seeded in a 96-well plate at a density of $1 \times 10^4$ cells per well and incubated for 24 hours, followed by the treatment with the polymer solutions of desired concentrations or the polyplexes/lipoplexes formed of carrier and siRNA. After additional 4 hours incubation, the plate was replaced by 112.5 µl fresh culture medium, and 12.5 µl MTT solution at the concentration of 5 mg/ml in PBS buffer was added into the cells for 6 hours. Viable cells were determined by measuring the absorbance of the samples at 570 nm (with 630 nm as the reference) using a SpectraMax M3 Multi-Mode Microplate Reader. Cell viabilities were calculated by comparison of the non-treated cells (normal cells) as 100%. The data were expressed as mean values (±standard deviations) of six experiments. Results of the experiments were shown in FIG. 24-25. For direct observation of cell growth states, COS-7 cells and SMMC-7721 cells were seeded in a 12-well plate at a density of $2 \times 10^5$ cells per well and incubated for 24 hours, followed by the treatment with the polymer solutions of desired concentrations. After additional 4 hours incubation, the plate was replaced by fresh culture medium and incubated for another 6 hours. The cell growth states were observed and recorded directly under a microscope. Results of the experiments were shown in FIG. 26.

Example 7

Figure 27:
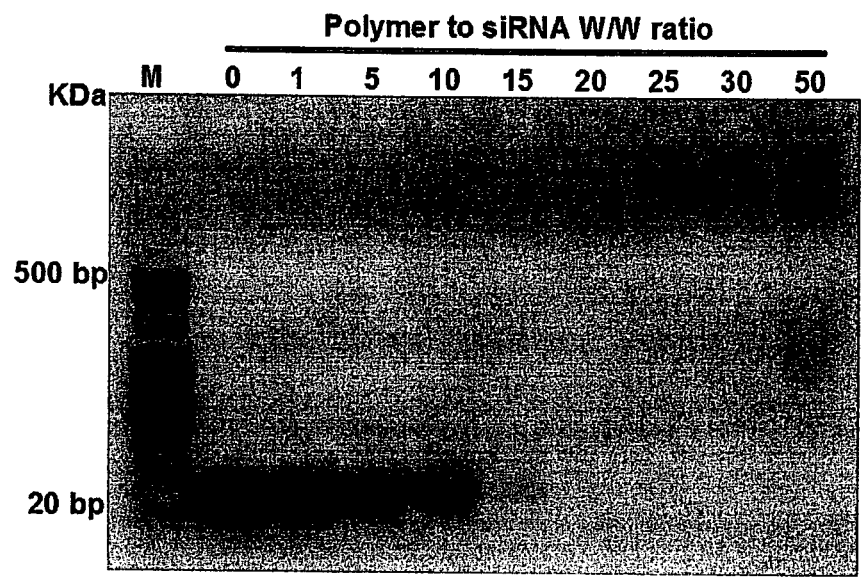
FIG. 27. Agarose gel electrophoresis of polyplexes formed of polyspermine imidazole-4,5-imine and siRNA at various polymer to nucleic acid ratios (W/W) in water.
Figure 28:
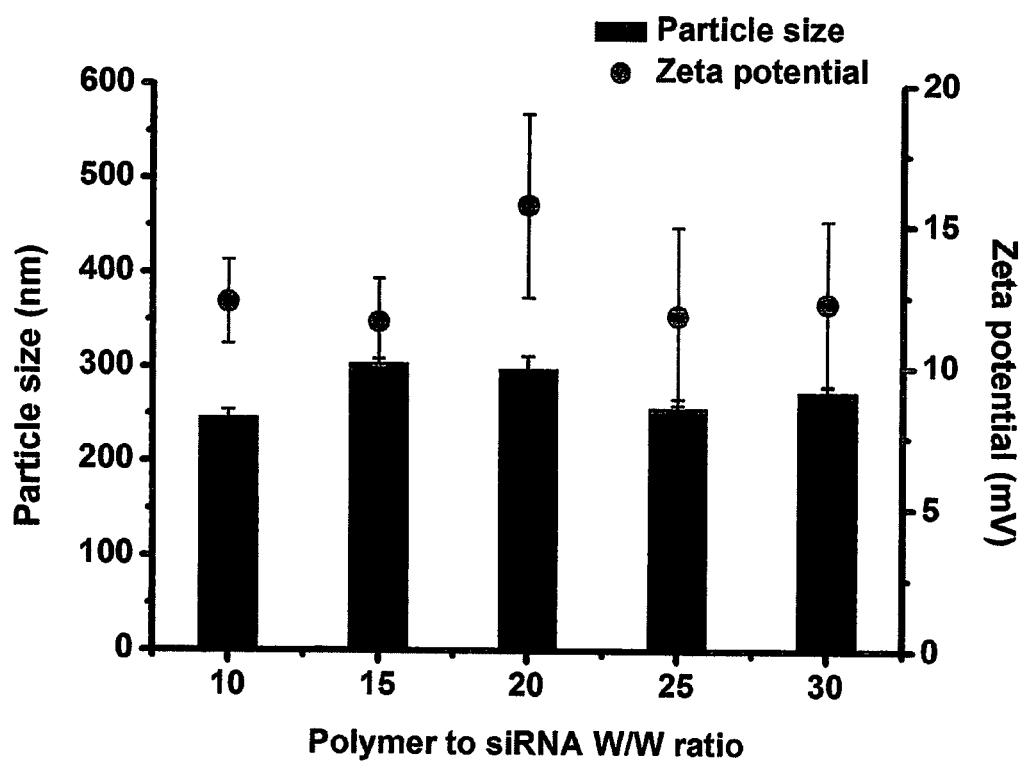
FIG. 28. Particle size and Zeta potential of polyplexes formed of polyspermine imidazole-4,5-imine and siRNA at various polymer to nucleic acid ratios (W/W) in water.
Figure 29:
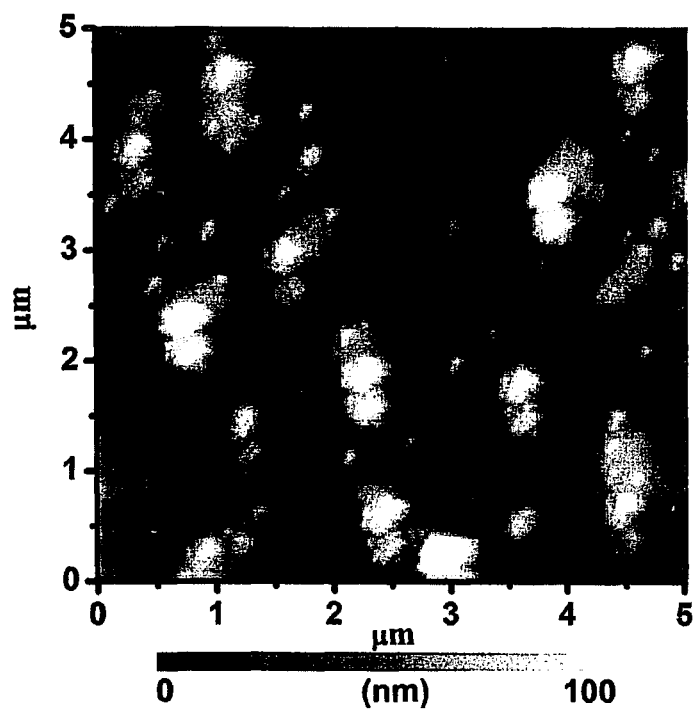
FIG. 29. AFM images of polyplexes formed of polyspermine imidazole-4,5-imine and siRNA at polymer to nucleic acid ratios (W/W) of 10.

Preparation and Characterization of Polyplexes Formed of Polyspermine Imidazole-4,5-Imine and Luciferase pGL3-Control siRNA Luciferase pGL3-control siRNA (Sense sequence: 5'-CUUACGCUGAGUACUUCGAtt-3'; Antisense sequence:

5'-UCGAAGUACUCAGCGUAAGtt-3') was obtained from QIAGEN Co., Ltd. All the materials used in this assay were RNase-free. Polyplexes were prepared by adding various concentrations of polyspermine imidazole-4,5-imine to siRNA to obtain the desired W/W ratio, followed by mixing gently for 30 s and incubated at room temperature for 30 mins. Polyplexes at various W/W ratios were loaded on 3.0% agarose gel in 1×TAE buffer containing 0.5 µg/ml ethidium bromide with 6× loading buffer and subjected to electrophoresis for 45 min at 110 V. The retardation of siRNA was visualized with a UV illuminator. Result of the experiment was shown in FIG. 27; The particle size and zeta potential of polyplexes at various W/W ratios were measured in water using a Brookhaven Instruments Corporation 90 Plus Particle Size Analyzer. The data were expressed as mean values (±standard deviations) of three experiments. Results of the experiments were shown in FIG. 28; The morphology of polyplexes at W/W ratio of 10 was also examined by AFM. Result of the measurement was shown in FIG. 29.

Example 8

Figure 30:
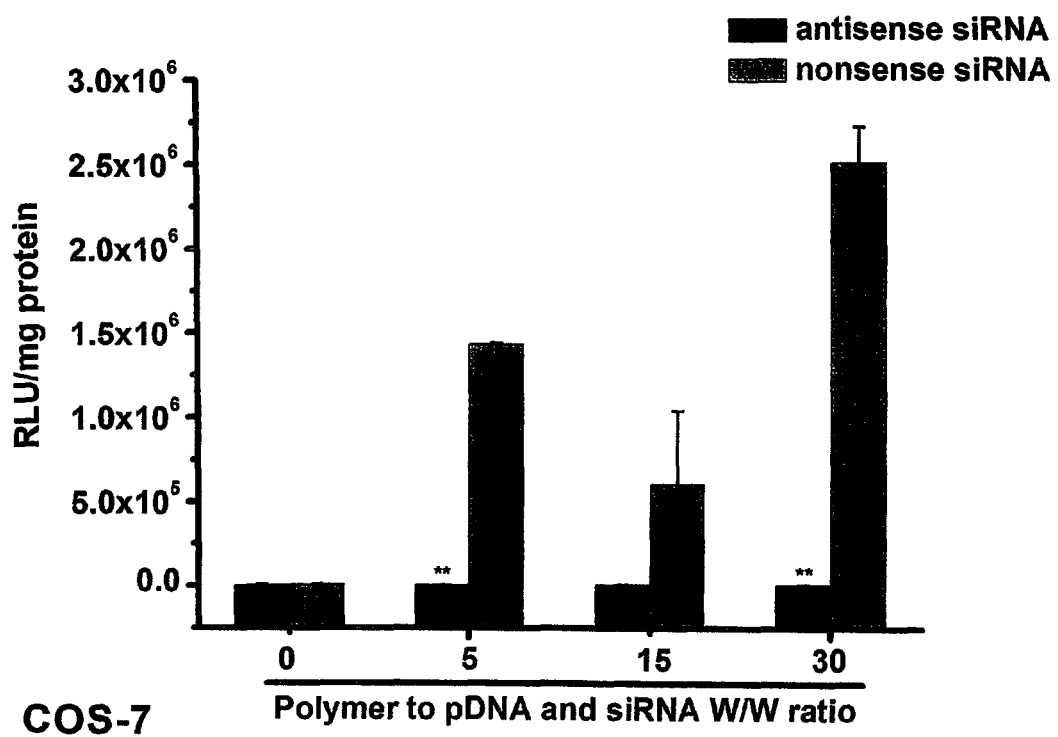
FIG. 30. Expression of luciferase gene by co-transfecting pDNA and siRNA (Blue: antisense; red: nonsense) into COS-7 cells using polyspermine imidazole-4,5-imine (*: P<0.05; **: P<0.01).
Figure 31:
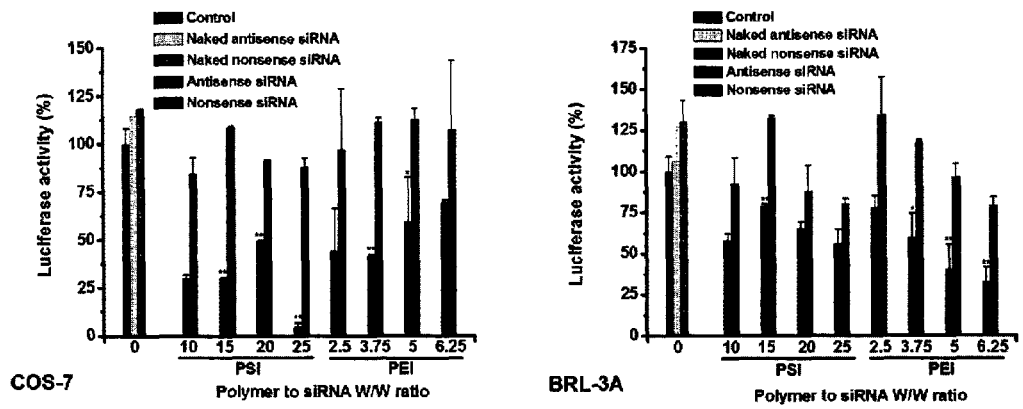
FIG. 31. Gene silencing activity of polyplexes formed of polyspermine imidazole-4,5-imine and siRNA at various polymer to nucleic acid ratios (W/W) (Blue: antisense; Red: nonsense) in COS-7 cells and BRL-3A cells pretreated with Lipofectamine 2000 and pDNA at polymer to nucleic acid ratio of 1 (*, P<0.05; **, P<0.01).
Figure 32:
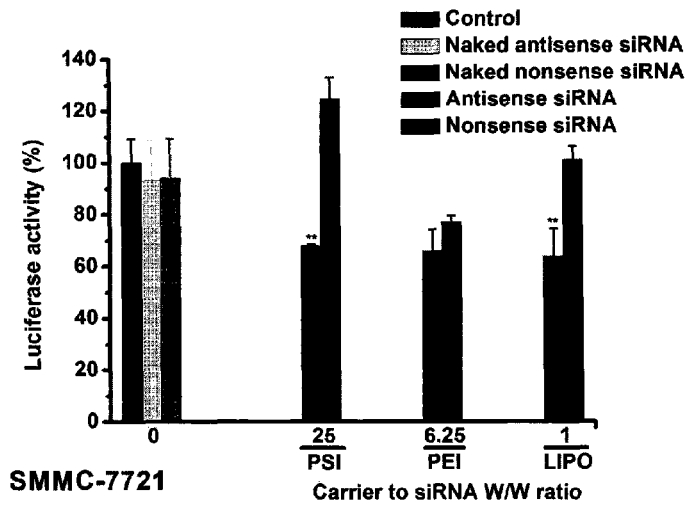
FIG. 32. Gene silencing activity of polyplexes formed of siRNA (Blue: antisense; Red: nonsense) with polyspermine imidazole-4,5-imine, PEI 25 KDa and Lipofectamine 2000 and (all at optimal polymer to gene ratio) in SMMC-7721 cells stably expressing the GL3 luciferase gene, as a control (*: P<0.05; **: P<0.01).

Gene Silencing Activity of Polyplexes Formed of Polyspermine Imidazole-4,5-Imine and Luciferase pGL3-Control siRNA in Vitro Luciferase pGL3-control siRNA and AllStars Negative Control siRNA (Cat. No. 1027280) were obtained from QIAGEN Co., Ltd. All the materials used in this assay were RNase-free. For co-transfection of pDNA with siRNA, COS-7 cells were seeded in a 48-well plate at a density of $5 \times 10^4$ cells per well to reach about 90% confluent at the time of transfection and incubated for 24 hours. pDNA (150 ng) and antisense siRNA (150 ng) or nonsense siRNA (150 ng) complexes formulated with polyspermine imidazole-4,5-imine at various W/W ratios were transfected into the cells for 4 hours in the OPTIMEM I medium. The transfection medium was replaced by fresh culture medium and further incubated for 48 hours. To determine the extent of luciferase gene expression, the transfected cells were washed with PBS solution and lysed with 1× cell lysis buffer followed by centrifugation at 12000 rpm for 3 min. 20 µl supernatant was mixed with 20 µl substrate and the luminescence was measured by a single tube luminometer. The protein concentrations of the samples were determined by Micro BCA™ Protein Assay Kit. Luciferase activity of a sample was expressed as relative light units (RLUs) normalized on protein concentration. Results of the measurements were shown in FIG. 30. For luciferase gene silencing activity assay, COS-7 cells and BRL-3A cells were seeded in a 48-well plate at a density of $5 \times 10^4$ cells per well. After the cells were treated with the lipoplexes formed of Lipofectamine 2000 and pDNA (150 ng) at W/W ratio of 1, antisense siRNA (150 ng) or nonsense siRNA (150 ng) complexes formulated with polyspermine imidazole-4,5-imine and PEI 25 KDa at various W/W ratios were transfected into the cells for 4 hours in the OPTIMEM I medium. The data were expressed as mean values (±standard deviations) of three experiments. Results of the measurements were shown in FIG. 31. In another case, SMMC-7721 cells stably expressing the GL3 luciferase gene were seeded in a 48-well plate at a density of $5 \times 10^4$ cells per well. antisense siRNA (150 ng) or nonsense siRNA (150 ng) complexes formulated with polyspermine imidazole-4,5-imine at W/W ratio of 25, PEI 25 KDa at W/W ratio of 6.25, and Lipofectamine 2000 at W/W ratio of 1 were transfected into the cells for 4 hours in the OPTIMEM I medium. The transfection medium was replaced by fresh culture medium and further incubated for 48 hours. To determine the extent of luciferase gene knockdown, the transfected cells were washed with PBS solution and lysed with 1× cell lysis buffer followed by centrifugation at 12000 rpm for 3 min. 20 µl supernatant was mixed with 20 µl substrate and the luminescence was measured by a single tube luminometer. The protein concentrations of the samples were determined by Micro BCA™ Protein Assay Kit. Luciferase activity of a sample was expressed as percent luminescence intensity compared to the untreated control normalized on protein concentration. The data were expressed as mean values (±standard deviations) of three experiments. Results of the measurements were shown in FIG. 32.

Example 9

Figure 33:
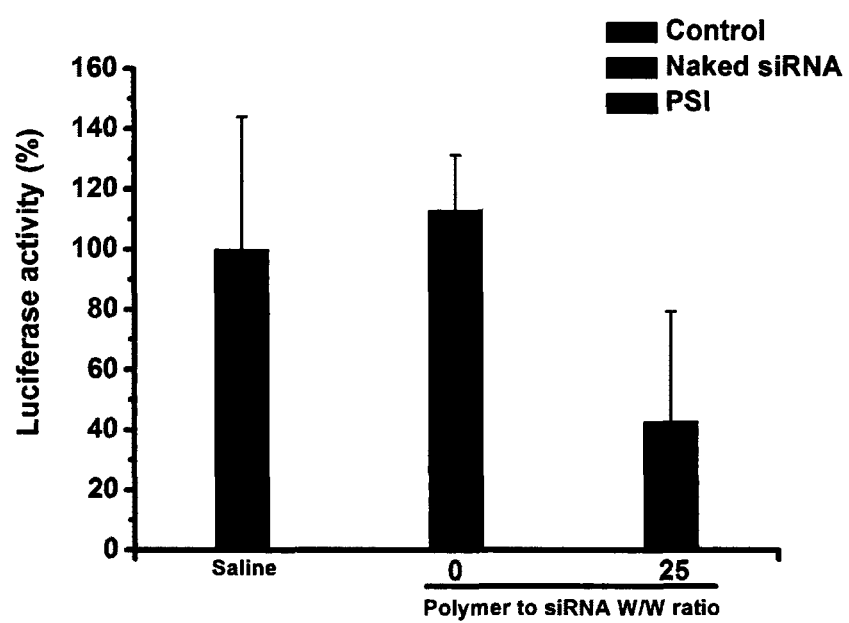
FIG. 33. Gene silencing activity of polyplexes formed of polyspermine imidazole-4,5-imine and siRNA at the optimal polymer to nucleic acid ratio in Male BALB/c-nu mice aged 6 weeks implanted with SMMC-7721 cells stably expressing the GL3 luciferase gene (naked siRNA and saline as the control).

Gene Silencing Activity of Polyplexes Formed of Polyspermine Imidazole-4,5-Imine and Luciferase pGL3-Control siRNA in Vivo Male BALB/c-nu mice aged 6 weeks were inoculated subcutaneously in the nape of the neck with $2 \times 10^6$ SMMC-7721 cells stably expressing the GL3 luciferase gene. All animal experiments were performed when the tumor reached 200-250 mm$^3$. Three weeks later, mice were given locally injections of polyplexes formed of polyspermine imidazole-4,5-imine and siRNA (10 µg) at W/W ratio of 25 formulated in 200 µl PBS buffer, naked siRNA (10 µg) formulated in 200 µl PBS buffer and 200 µl saline was injected as control. After 48 hours, the mice were euthanized and the tumors were taken out, washed with cold saline and collected. The tumors were ground in liquid nitrogen and homogenized in 1 ml 5× cell lysis buffer, followed by centrifugation at 12000 rpm for 3 min. 20 µl supernatant was mixed with 20 µl substrate and the luminescence was measured by a single tube luminometer. The protein concentrations of the samples were determined by a protein assay kit. Luciferase activity of a sample was normalized with the protein content and expressed as percent luminescence intensity compared to the untreated control. The data were expressed as mean values (±standard deviations) of six experiments. Result of the measurement was shown in FIG. 33.

REFERENCES

[1] Mulligan, R. C.; The basic science of gene therapy. Science, 1993, 260, 926-932.

[2] Pack, D. W.; Hoffman, A. S.; Pun, S.; Stayton, P.; Design and development of polymers for gene delivery. Nature Reviews Drug Discovery, 2005, 4, 581-593.

[3] Luo, D.; Saltzman, W. M.; Synthetic DNA delivery system. Nature Biotechnology, 2000, 18, 33-37.

[4] Xu, Y.; Azoka, Jr. F. C.; Mechanism of DNA release from cationic liposome/DNA complex used in cell transfection. Biochemistry, 1996, 35, 5616-5623.

[5] Abdelhady, H. G.; et al.; Direct real-time molecular scale visualization of the degradation of condensed DNA complexes exposed to DNase I. Nucleic Acids Research, 2003, 31, 4001-4005.

[6] Wolff, J. A.; Rozema, D. B.; Breaking the bonds: nonviral vectors become chemically dynamic. Molecular Therapy, 2008, 16 (1), 8-15.

[7] Yokoyama, M.; Gene delivery using temperature responsive polymeric carriers. Drug Discovery Today, 2002, 7, 426-432.

[8] Schaffer, D. V.; Fidelman, N. A.; Dan, N.; Lauffenberger, D. A.; Vector unpacking as a potential barrier for receptor-mediated polyplex gene delivery. Biotechnology and Bioengineering, 2000, 67, 598-606.

[9] Hinrichs, W. L. J.; et al.; Thermosensitive polymers as carries for DNA delivery. Journal of Controlled Release, 1999, 60, 249-259.

[10] Lim, Y. L.; Kim, S.; Suh, H.; Park, J.; Biodegradable, endosome disruptive, and cationic network-type polymer as a highly efficient and nontoxic gene delivery carrier. Bioconjugate Chemistry, 2002, 13, 952-957.

[11] Lim, Y. L.; et al.; Biodegradable Polyester, Poly[α-(4-Aminobutyl)-L-glycolic acid], as a Non-Toxic Gene Carrier. Pharmaceutical Research, 2000, 17, 811-816.

[12] Forrest, M. L.; Koerber, J. T.; Pack, D. W.; A degradable polyethylenimine derivative with low toxicity for highly efficient gene delivery. Bioconjugate Chemistry, 2003, 14, 934-940.

[13] Gosselin, M. A.; Guo, W.; Lee, R. J.; Efficient gene transfer using reversibly cross-linked low molecular weight polyethylenimine. Bioconjugate Chemistry, 2001, 12, 989-994.

[14] Baker, A.; et al.; Polyethylenimine (PEI) is a simple, inexpensive and effective reagent for condensing and linking plasmid DNA to adenovirus for gene delivery. Gene Therapy, 1997, 4 (8), 773-782.

[15] Jin, T; Du, Zixiu; Polycationic gene carriers formed of endogenous amino group bearing monomers. WO2009/100,645.

What is claim is:

1. A cationic polymer formed of amino group-bearing monomers and heterogeneous aromatic bis- or di-aldehyde linkers, bound through conjugated imine linkages, wherein,
    a) the amino group-bearing molecules possess three or more amino groups, wherein at least two of the amino groups are primary amines to ensure the formation of a cationic polyimine;
    b) the heterogeneous aromatic bis- or di-aldehydes have a pKa below 7; and
    c) an aromatic ring of the heterogeneous aromatic bis- or di-aldehyde linkers is incorporated within the structure of the conjugated imine linkages.

2. The cationic polymer of claim 1, wherein the amino group-bearing monomers are selected from the group consisting of spermine, spermidine, low molecular weight polyethylene imine (PEI), and derivatives or analogues thereof.

3. The cationic polymer of claim 1, wherein an aromatic ring within the heterogeneous aromatic bis- or di-aldehyde linkers is an imidazole, a pyrazole, a pyridine, or a pyrimidine ring.

4. The cationic polymer of claim 3, wherein the imidazole, pyrazole, pyridine, or pyrimidine is conjugated in the polyimine.

5. The cationic polymer of claim 1, wherein the bis- or di-aldehydes are imidazole-4,5-bisaldehyde, imidazole-2,5-bisaldehyde, pyrazole-3,4-bisaldehyde, pyrazole-3,5-bisaldehyde, pyridine substituted with two formic aldehydes on the heterocyclic ring or pyrimidine substituted with two formic aldehydes on the heterocyclic ring.

6. The cationic polymer of claim 1, wherein an imine linkage between the amino group-bearing monomers and the heterogeneous aromatic bis- or di-aldehyde linkers comprises two imines (bis-imine or di-imine) and a heterocyclic ring which are all associated through a conjugated π bond.

7. The cationic polymer of claim 6, wherein the heterocyclic ring contains nitrogen or nitrogens.

8. The cationic polymer of claim 7, wherein the heterocyclic ring containing nitrogen or nitrogens is imidazole, pyrazole, pyridine or pyrimidine.

9. The cationic polymer of claim 1, wherein cleavable bonds are formed by reaction between said amino group-bearing monomers with the heterogeneous aromatic bis- or di-aldehyde linkers.

10. The cationic polymer of claim 1, having a molecular weight of 10000 daltons or over.

11. A method for synthesizing the cationic polymer of claim 1, comprising reacting an amino group-bearing monomer and a linker molecule possessing two or more reactive aldehyde groups.

12. The method of claim 11, wherein the ratio of the amino group-bearing monomer to the linker is in the range of 0.9/1.1 to 1.1/0.9.

* * * * *